United States Patent [19]

Schinzel

[11] Patent Number: 4,675,402

[45] Date of Patent: Jun. 23, 1987

[54] PROCESS FOR THE PREPARATION OF DIALKOXYTRIAZINYLPYRENES

[75] Inventor: Erich Schinzel, Hofheim am Taunus, Fed. Rep. of Germany

[73] Assignee: Hoechst Aktiengesellschaft, Fed. Rep. of Germany

[21] Appl. No.: 783,426

[22] Filed: Oct. 3, 1985

[30] Foreign Application Priority Data

Oct. 13, 1984 [DE]  Fed. Rep. of Germany ....... 3437663

[51] Int. Cl.$^4$ .......................................... C07D 251/20
[52] U.S. Cl. .................................................. 544/219
[58] Field of Search ......................................... 544/219

[56] References Cited

FOREIGN PATENT DOCUMENTS 1273479  3/1969  Fed. Rep. of Germany .
985484   3/1965  United Kingdom .

Primary Examiner—John M. Ford
Attorney, Agent, or Firm—Connolly and Hutz

[57] ABSTRACT

The process for the preparation of 2,4-di-($C_1$–$C_4$)-alkoxy-1,3,5-triazinyl-6-pyrenes by reacting 2,4-dichloro-1,3,5-triazinyl-6-pyrene with alkali metal ($C_1$–$C_4$)-alcoholates is carried out in a mixture of a lower alkanol and an aprotic, dipolar organic solvent. The product, which is of importance as an optical brightener, is obtained in an improved state of purity as a result of using this mixture of solvents, and higher degrees of whiteness are obtained thereby.

4 Claims, No Drawings

PROCESS FOR THE PREPARATION OF DIALKOXYTRIAZINYLPYRENES

The preparation of 2,4-dialkoxy-1,3,5-triazinyl-6-pyrenes by reacting 2,4-dichloro-1,3,5-triazinyl-6-pyrene with sodium alcoholates in the corresponding alkanol has already been disclosed in DE-B 1,273,479 (=GB-A 985,484). These compounds have acquired practical importance as optical brighteners.

It has now been found that 2,4-dialkoxy-1,3,5-triazinyl-6-pyrenes can be obtained in a higher state of purity and with an improved brightening action if the reaction of the 2,4-dichloro-1,3,5-triazinyl-6-pyrene with alcoholates is carried out in a mixture of a lower alkanol and an aprotic, dipolar organic solvent.

The invention relates, therefore, to a process for the preparation of 2,4-di-($C_1$-$C_4$)-alkoxy-1,3,5-triazinyl-6-pyrenes by reacting 2,4-dichloro-1,3,5-triazinyl-6-pyrene with alkali metal ($C_1$-$C_4$)-alcoholates, which comprises carrying out the reaction in a mixture of a lower alkanol and an aprotic, dipolar organic solvent, and, if necessary, purifying the resulting product by subjecting it to after-treatment with this aprotic, dipolar organic solvent.

The following may be mentioned as aprotic, dipolar organic solvents: dimethylformamide, dimethylacetamide, tetramethylurea, hexamethylphosphoric acid triamide, dimethyl sulfoxide and, in particular, N-methylpyrrolidone (=NMP). Suitable lower alkanols are, in particular, ($C_1$-$C_4$)-alkanols, ie. methanol, ethanol, n-propanol, isopropanol and n-, iso- and tert.-butanol. 400 to 900 parts by weight, preferably 500 to 600 parts by weight, of the aprotic, dipolar organic solvent are used for 100 parts by weight of the lower alkanol.

In the process according to the invention, the crude 2,4-dichloro-1,3,5-triazinyl-6-pyrene is initially taken in a mixture of the lower alkanol and the aprotic, dipolar organic solvent, at 15° to 20° C., and 2.0 to 2.4 moles of an alkali metal ($C_1$-$C_4$)-alcoholate (if appropriate dissolved in the lower alkanol) are introduced or added dropwise to the stirred reaction mixture. The alcoholate solution is preferably prepared by dissolving 2.0 to 2.4 gram atoms of metallic sodium in the lower alkanol. The reaction mixture is stirred at 15° to 20° for a further 15 to 20 hours until 2,4-dichloro-1,3,5-triazinyl-6-pyrene or 2-chloro-4-($C_1$-$C_4$)-alkoxy-1,3,5-triazinyl-6-pyrene can no longer be detected in a thin layer chromatogram. After being cooled in an ice bath, the mixture is worked up in the customary manner.

Particularly pure products are obtained if the 2,4-di-($C_1$-$C_4$)-alkoxy-1,3,5-triazinyl-6-pyrene prepared by the above procedure is stirred at temperatures of up to about 100° with the aprotic, dipolar organic solvent used in the reaction and, after being cooled in an ice bath, is filtered off with suction and rinsed.

The distinguishing feature of 2,4-di-($C_1$-$C_4$)-alkoxy-1,3,5-triazinyl-6-pyrenes, in particular the 2,4-dimethoxy compound, if they are prepared by the process according to the invention, is that they have an excellent brightening action on polyester. Very brilliant, reddish-tinged white shades are obtained in this way, particularly under thermosol conditions.

EXAMPLE 1

105 g (0.3 mole) of 2,4-dichloro-1,3,5-triazinyl-6-pyrene (a crude product of melting point 258° to 260.5°, sinters at 256°) are introduced into a mixture, cooled to 15°, of 90 g of methanol and 540 g of NMP; the resulting mixture is homogenized by being stirred for 30 minutes. 35.6 g (=0.66 mole) of sodium methylate powder are added at 15° to 20° in the course of about 1 hour. The mixture is stirred for a further 17 hours at this temperature and is then cooled in an ice bath for 1 hour, and the precipitated reaction product is filtered off with suction. It is washed free from chloride ions with NMP and methanol and then with hot water. After drying, 81.1 g of 2,4-di-methoxy-1,3,5-triazinyl-6-pyrene of melting point 197° to 198° are obtained, corresponding to 79.2% of theory.

The above product is purified further by stirring it with 360 g of NMP at about 100°, filtering it off again with suction, after cooling in an ice bath, and rinsing it with NMP and methanol. The result of this purification is to raise the melting point to 198° to 199°.

EXAMPLE 2

A portion of fabric composed of polyester staple fibers is washed, dried and padded, in a customary manner, on a padder with an aqueous dispersion containing 1.0 g/liter of 2,4-dimethoxy-1,3,5-triazinyl-6-pyrene of melting point 198° to 199° (in accordance with Example 1). The material is squeezed between rollers by means of a padder so that a liquor pick-up of 55% results. This corresponds to an absorption of optical brightener on the goods of 0.055%. The material thus padded is then dried on a tenter for 30 seconds at 120° C. and is subjected to thermosol treatment at 190° C. for a further 30 seconds. The following degrees of whiteness are obtained in this procedure:

Berger degree of whiteness: 175
Stensby degree of whiteness: 170

Using a grade of 2,4-dimethoxy-1,3,5-triazinyl-6-pyrene prepared by the process disclosed in DE-B 1,273,479 from a grade of 2,4-dichloro-1,3,5-triazinyl-6-pyrene which has been purified by reprecipitation, the following degrees of whiteness are obtained under the same conditions:

Berger degree of whiteness: 168
Stensby degree of whiteness: 165

I claim:

1. In a process for the preparation of 2,4-di-($C_1$-$C_4$)-alkoxy-1,3,5-triazinyl-6-pyrenes by reacting 2,4-dichloro-1,3,5-triazinyl-6-pyrene with alkali metal ($C_1$-$C_4$)-alcoholates in the presence of a lower alkanol, the improvement which comprises:

carrying out the reaction in a mixture of a lower alkanol and an aprotic, dipolar organic solvent selected from the group consisting of dimethylformamide, dimethylacetamide, tetramethylurea, hexamethylphosphoric acid triamide, dimethyl sulfoxide and N-methylpyrrolidone.

2. The process as claimed in claim 1, wherein the reaction product obtained is 2,4-dimethoxy-1,3,5-triazinyl-6-pyrene.

3. The process as claimed in claim 1, wherein the aprotic, dipolar organic solvent used is N-methylpyrrolidone.

4. The process as claimed in claim 1, wherein the reaction product obtained is purified by subjecting it to after-treatment with a said aprotic, dipolar organic solvent.

* * * * *